(12) United States Patent
Husmark et al.

(10) Patent No.: US 12,053,360 B2
(45) Date of Patent: Aug. 6, 2024

(54) ABSORBENT ARTICLE WITH SKIN PH-ADJUSTING EFFECT

(71) Applicant: Essity Hygiene and Health Aktiebolag, Gothenburg (SE)

(72) Inventors: Ulrika Husmark, Gothenburg (SE); Chatrine Stridfeldt, Gothenburg (SE)

(73) Assignee: ESSITY HYGIENE AND HEALTH AKTIEBOLAG, Goteborg (CH)

( * ) Notice: Subject to any disclaimer, the term of this patent is extended or adjusted under 35 U.S.C. 154(b) by 1130 days.

(21) Appl. No.: 16/612,987

(22) PCT Filed: Jun. 7, 2017

(86) PCT No.: PCT/EP2017/063811
§ 371 (c)(1),
(2) Date: Nov. 12, 2019

(87) PCT Pub. No.: WO2018/224140
PCT Pub. Date: Dec. 13, 2018

(65) Prior Publication Data
US 2020/0170854 A1    Jun. 4, 2020

(51) Int. Cl.
A61F 13/84    (2006.01)
A61F 13/511   (2006.01)
A61L 15/20    (2006.01)
A61L 15/22    (2006.01)

(52) U.S. Cl.
CPC .... *A61F 13/8405* (2013.01); *A61F 13/51113* (2013.01); *A61L 15/20* (2013.01); *A61L 15/22* (2013.01); *A61F 2013/8402* (2013.01); *A61F 2013/8411* (2013.01)

(58) Field of Classification Search
CPC ............ A61F 13/8405; A61F 13/51113; A61F 2013/8402; A61F 2013/8411; A61F 2013/51117; A61L 15/20; A61L 15/22
See application file for complete search history.

(56) References Cited

U.S. PATENT DOCUMENTS

| | | | |
|---|---|---|---|
| 4,685,909 A | 8/1987 | Berg et al. | |
| 6,103,954 A * | 8/2000 | Grondin | A61F 13/53747 604/378 |
| 2003/0082970 A1 * | 5/2003 | Moberg-Alehammar | A61K 8/0208 442/59 |
| 2007/0021951 A1 | 1/2007 | Lee Seislink | |
| 2007/0213412 A1 * | 9/2007 | Bacon | A61L 15/48 516/53 |
| 2011/0297185 A1 | 12/2011 | Godin et al. | |
| 2012/0115718 A1 | 5/2012 | Nakashita et al. | |

FOREIGN PATENT DOCUMENTS

| | | | | |
|---|---|---|---|---|
| CN | 101032513 A | 9/2007 | | |
| CN | 101095651 A | 1/2008 | | |
| CN | 105968391 A | 9/2016 | | |
| JP | S61-179155 A | 8/1986 | | |
| JP | S62-028402 A | 2/1987 | | |
| JP | 2002-029978 A | 1/2002 | | |
| JP | 2003-119150 A | 4/2003 | | |
| JP | 2003-512894 A | 4/2003 | | |
| JP | 2003-516778 A | 5/2003 | | |
| JP | 2003-517882 A | 6/2003 | | |
| JP | 2007-525313 A | 9/2007 | | |
| JP | 2011-019566 A | 2/2011 | | |
| WO | 00/59556 A2 | 10/2000 | | |
| WO | 0132226 A1 | 5/2001 | | |
| WO | 0135885 A1 | 5/2001 | | |
| WO | WO-0132226 A1 * | 5/2001 | ............. | A61L 15/20 |
| WO | 0145615 A1 | 6/2001 | | |
| WO | 2004/037305 A1 | 5/2004 | | |
| WO | 2004108177 A1 | 12/2004 | | |
| WO | 2016148612 A1 | 9/2016 | | |
| WO | WO-2016148612 A1 * | 9/2016 | ............. | A61F 13/511 |

OTHER PUBLICATIONS

Office Action (Decision to Grant) issued on Sep. 25, 2020, by the Federal Service for Intellectual Property in Russian Patent Application No. 2019139396/12(077474) and an English Translation of the Office Action. (8 pages).
International Preliminary Report on Patentability for International Application No. PCT/EP2017/063811, dated Dec. 10, 2019, 6 pages.
Office Action issued on Apr. 15, 2020, by the Australian Government/ IP Australia in corresponding Australian Patent Application No. 2017417540. (4 pages).
Office Action (Decision on Grant) issued on Jun. 19, 2020, by the Federal Service for Intellectual Property in Russian Patent Application No. 2019139396/03(077474), and an English Translation of the Office Action. (13 pages).
Office Action No. 3737 issued on Apr. 20, 2021, by the Colombian Patent Office in Colombian Patent Application No. NC2019/ 0013785 and an English Translation of the Office Action. (16 pages).
Office Action (Notification of the First Office Action) issued on Mar. 23, 2021, by the China National Intellectual Property Administration in corresponding Chinese Patent Application No. 201780090688. 9, and an English Translation of the Office Action. (26 pages).
Office Action (Notice of Acceptance for patent application) issued on Oct. 9, 2020 by the Australian Government-IP Australia in corresponding Australian Patent Application No. 2017417540. (3 pages).

(Continued)

*Primary Examiner* — Susan S Su
(74) *Attorney, Agent, or Firm* — BUCHANAN INGERSOLL & ROONEY PC

(57) ABSTRACT

A disposable absorbent hygiene article is provided, comprising a liquid permeable topsheet, a backsheet and an absorbent core disposed between the topsheet and the backsheet. In the article, at least one layer, selected from said topsheet and an optionally present liquid permeable and nonabsorbent layer disposed between said topsheet and said absorbent core, is provided with a dry coating comprising at least one lactone selected from the group consisting of γ- and δ-lactones.

27 Claims, No Drawings

(56) References Cited

OTHER PUBLICATIONS

Office Action (Communication pursuant to Article 94(3) EPC) issued on Nov. 16, 2020, by the European Patent Office in corresponding European Application No. 17 728 211.8-1102, (5 pages).
International Search Report and Written Opinion for International Application No. PCT/EP2017/063811, dated Jan. 9, 2018, 9 pages.
Lambers et al., "Natural Skin Surface pH is on Average Below 5, Which is Beneficial for its Resident Flora", International Journal of Cosmetic Science, 2006, 28, pp. 359-370.
Office Action (Notification of the second Office Action) issued on Sep. 3, 2021 by the China National Intellectual Property Administration (CNIPA) of the People's Republic of China in corresponding Chinese Patent Application No. 201780090688.9, and an English Translation of the Office Action. (22 pages).
Office Action issued on Aug. 27, 2021, by the Colombian Patent Office in Colombian Patent Application No. NC2019/0013785, (23 pages).
Office Action (Notice of Reasons for Rejection) issued on Apr. 5, 2021, by the Japanese Patent Office in corresponding Japanese Patent Application No. 2019-567527, and an English Translation of the Office Action. (34 pages).
Office Action issued on Jul. 6, 2022, by the Colombian Patent Office in corresponding Colombian Patent Application No. NC 2019/0013785, and an English Translation of the Office Action. (24 pages).
Office Action (Decision of Rejection) issued on Jun. 23, 2022, by the Chinese Patent Office in corresponding Chinese Patent Application No. 201780090688.9, and an English Translation of the Office Action. (19 pages).

\* cited by examiner

ABSORBENT ARTICLE WITH SKIN PH-ADJUSTING EFFECT

CROSS REFERENCE TO RELATED APPLICATIONS

This is a U.S. National Phase application of PCT/EP2017/063811, filed Jun. 7, 2017, the disclosure of which is incorporated herein by reference in its entirety for all purposes.

TECHNICAL FIELD

The present disclosure relates to a disposable absorbent hygiene article, comprising a liquid permeable topsheet, a backsheet and an absorbent core disposed between the topsheet and the backsheet wherein at least one layer, selected from said topsheet and an optionally present liquid permeable and nonabsorbent layer disposed between said topsheet and said absorbent core, is provided with a dry coating.

BACKGROUND

Absorbent articles of the kind to which this disclosure relates, e.g. diapers for children as well as for adults, incontinence shields, sanitary napkins and panty liners, are adapted to be worn against the skin in or near the crotch region with the purpose of absorbing body exudates such as urine, faeces, liquid discharge and/or menstrual fluid. Such absorbent articles conventionally comprise a liquid permeable topsheet layer, an absorbent core and a backsheet layer.

Uses of products that are applied in direct contact with the skin may lead to unwanted side-effects. These may occur because of occlusion, moisture, mechanical, microbial, and enzymatic factors which all, to different degrees, interact and amplify the influence of each other and may cause different forms of skin irritation and primary or secondary skin infections which sometimes occur in users of said articles. An increase in pH is a normal phenomenon during use of sanitary articles in contact with skin. It has been demonstrated that skin with pH values below 5.0 is in a better condition than skin with pH values above 5.0. This has been shown by measuring the biophysical parameters of barrier function, moisturization and scaling. The effect of pH on adhesion of resident skin microflora has also been assessed and it has been shown that an acid skin pH (4-4.5) keeps the resident bacterial flora attached to the skin, whereas an alkaline pH (8-9) promotes the dispersal from the skin, see e.g. Lambers H et al (2006), Natural skin surface pH is on average below 5, which is beneficial for its resident flora. *Int J Cosmet Sci,* 28 (5), 359-70.

Another example of unwanted effects of using absorbent articles in contact with the skin is the increased activity of enzymes such as lipases and proteases which exhibit a strongly pH-dependent activity which increases with increasing pH. With the increased enzyme activity, the skin starts to decompose and becomes sensitive to mechanical forces and bacterial attacks. Absorbent articles comprising acidifying agents incorporated to control the pH of the skin in contact with the sanitary article are generally known in the art. The acidifying agents may be applied in lotions or in aqueous solutions. An absorbent article impregnated with a lotion may suffer from an impaired absorbency. The lotion application step may also lead to complications in a production process.

Application of the acidifying agent in an aqueous form may have less impact on the absorbency of the sanitary article. However, there are also other aspects to take into account in terms of efficacy of the added agent during the use of a sanitary article, a simple and well-functioning application process as well as ensuring a long shelf life, i.e. storage stability.

Lactic acid has been used in topsheet treatments of absorbent articles. The pH effect of the lactic acid has however shown a tendency to decrease with time during storage of the articles before use, leading to a shortened shelf life.

There is therefore still a need in the art for improved absorbent hygiene articles exhibiting a low pH on a body-facing surface.

SUMMARY

The present disclosure relates inter alia to a disposable absorbent hygiene article having a skin beneficial effect and which provides a long shelf life.

The present inventors have found that by providing the topsheet, or a layer between the topsheet and the absorbent core, of such an article with a dry coating comprising at least one lactone selected from the group consisting of γ- and δ-lactones, the above objects are at least partially met.

Therefore, according to one aspect, the present disclosure relates to a disposable absorbent hygiene article comprising a liquid permeable topsheet, a backsheet and an absorbent core disposed between the topsheet and the backsheet, wherein at least one layer, selected from said topsheet and an optionally present liquid permeable and nonabsorbent layer, disposed between said topsheet and said absorbent core, is provided with a dry coating comprising at least one lactone selected from the group consisting of γ- and δ-lactones.

In another aspect, the present disclosure relates to a method for the manufacture of a disposable absorbent hygiene article comprising disposing an absorbent core between a liquid permeable topsheet and a backsheet, and optionally disposing a liquid permeable and nonabsorbing layer between said topsheet and said absorbent core, wherein at least one of said topsheet and said liquid permeable and nonabsorbing layer disposed between said topsheet and said absorbent core is provided with a dry coating comprising at least one lactone selected from the group consisting of γ- and δ-lactones.

In yet another aspect, the present disclosure, relates to the use of a disposable absorbent hygiene article to adjust or maintain the pH of the skin in contact with the article to a value of from 3.5 to 5.5.

In yet another aspect, the present disclosure relates to the topsheet material as such, i.e. a liquid permeable web material, having a dry coating comprising at least one lactone selected from the group consisting of γ- and δ-lactones.

These and other aspects of the invention will be further explained below.

DETAILED DESCRIPTION OF PARTICULAR EMBODIMENTS

In a first aspect, the present disclosure relates to a disposable absorbent hygiene article, comprising a liquid permeable topsheet, a backsheet and an absorbent core disposed between the topsheet and the backsheet.

The article defines a body facing side, intended to be placed against or towards the skin of the wearer, and an opposite, garment facing side, with the topsheet typically being the outermost layer at the bodyfacing side.

In the article, at least one layer selected from said topsheet and an optionally present liquid permeable and nonabsorbent layer disposed between said topsheet and said absorbent core is provided with a dry coating comprising at least one lactone selected from the group consisting of γ- and δ-lactones.

As used herein, the term "disposable absorbent hygiene article" refers to products that are intended to be placed against the skin of the wearer to absorb and contain body exudates, such as urine, faeces and menstrual fluid. The disclosure refers to disposable articles, i.e. articles that are not intended to be laundered or otherwise restored or reused as a sanitary article. Examples of disposable absorbent articles include feminine hygiene products such as sanitary napkins, panty liners, sanitary panties and feminine inserts; diapers and pant diapers for infants and incontinent adults; incontinence pads; diaper inserts and the like.

The liquid permeable topsheet can be any suitable topsheet material as known by the person skill d in the art and may be fibrous topsheet material composed of a nonwoven material, e.g. spunbonded, meltblown, carded, hydroentangled, wetlaid, etc. Suitable nonwoven materials can be composed of natural fibers, such as woodpulp or cotton fibres, synthetic thermoplastic fibers, such as polyolefins, polyesters, polyamides and blends and combinations thereof or from a mixture of natural and synthetic fibers. The topsheet material may essentially constitute of non-absorbent fibers, such as synthetic thermoplastic fibers, such as such as polyolefins, polyesters, polyamides and blends and combinations thereof. The synthetic fibers may be monocomponent fibers, bicomponent fibers or multicomponent fibers comprising polyesters, polyamides and/or polyolefins such as polypropylene and polyethylene. It is contemplated that a nonwoven material used as a topsheet in accordance with the present disclosure may be a single layer or multilayered material. Examples of the latter including for example combinations of spunbonded and meltblown fibres, commonly referred to as SMS (spunbond-meltblown-spunbond), SMMS (spunbond-meltblown-meltblown-spunbond) as well as other multilayered nonwoven materials.

The topsheet material may alternatively be a perforated plastic film, i.e. a plastic film provided with a plurality of openings or holes allowing liquid to pass from one side of the film to the other side of the film through the openings. Further examples of topsheet materials are porous foams.

The materials suited as topsheet materials should be soft and non-irritating to the skin and be readily penetrated by body fluid, such as urine or menstrual fluid.

The topsheet may have a dry basis weight of from 10 to 50 $g/m^2$, such as from 15 $g/m^2$ to 50 $g/m^2$, such as from 15 $g/m^2$ to 30 $g/m^2$, for example from 15 $g/m^2$ to 25 $g/m^2$.

A topsheet having an open structure has been found to contribute to further reducing the wetting zone leading to a prolonged skin beneficial effect when used in a sanitary article in accordance with the present disclosure. The topsheet may furthermore be of a structure which do not promote wicking in X-Y direction, such as a uniform, even and non-corrugated structure. The topsheet may also comprise or consist essentially of non-absorbent fibers.

The backsheet may consist of a thin plastic film, e.g. a polyethylene or polypropylene film, or a nonwoven material coated with a liquid impervious material, a hydrophobic nonwoven material, which resists liquid penetration. Laminates of plastic films and nonwoven materials may also be used. In an embodiment, the backsheet material is vapor permeable, breathable, so as to allow vapor to escape from the absorbent structure, while still preventing liquids from passing through the backsheet material, i.e. being liquid impermeable and vapor permeable.

The absorbent hygiene article according to this disclosure comprises an absorbent structure, the absorbent core, arranged between the topsheet and the backsheet. The absorbent core can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbents in an absorbent structure. It is also common to have absorbent structures comprising layers of different material with different properties with respect to liquid acquisition capacity, liquid distribution capacity and storage capacity. This is well-known to the person skilled in the art and does therefore not have to be described in detail. The thin absorbent bodies, which are common in today's sanitary articles, often comprise a compressed mixed or layered structure of cellulosic fluff pulp and superabsorbent. For the purpose of the present disclosure, the term "absorbent core" in its broadest meaning also include liquid retaining structures which retains liquid by means of capillary forces, such as open cell porous structures, such as foams, and high loft materials of synthetic fibers.

Absorbent cores for use in absorbent products in accordance with the present disclosure may comprise superabsorbent polymers or may essentially or completely free from superabsorbent polymers. If superabsorbent polymers are present, such may be present at an amount of example contain from 10, such as from 25, for example from 40, to 100, such as to 80, for example to 75 wt % superabsorbents, based on the total weight of the absorbent core.

The size and absorbent capacity of the absorbent core may be varied to be suited for different uses such as sanitary napkins, pantyliners, adult incontinence pads and diapers, baby diapers, pant diapers, etc.

The body facing surface of the absorbent core may abut, be in direct contact with, the garment facing surface of the topsheet.

Alternatively, the hygiene absorbent article in accordance with the present disclosure may comprise further layers in addition to the topsheet, backsheet and absorbent core, as is well known in the art. For example, a liquid permeable and nonabsorbing layer, herein also referred to as the "intermediate layer" may be disposed between the absorbent core and the topsheet, over at least part of the bodyfacing surface of the absorbent core. A lactone-containing dry coating, as discussed herein, comprising at least one lactone being selected from γ- and δ-lactones may be applied to said liquid permeable and nonabsorbing layer and/or on the topsheet.

The intermediate layer may abut the topsheet, i.e. the bodyfacing surface of that layer may be in contact with the garment facing surface of the topsheet. The intermediate layer may abut the absorbent core, i.e. the garment facing surface of that layer may be in contact with the body facing surface of the topsheet. The intermediate layer may abut the absorbent core and the topsheet.

The intermediate layer may be a porous fibrous layer, such as a nonwoven material, essentially consisting of non-absorbent fibers, and may be referred to as an acquisition layer.

The presence of an intermediate layer in accordance with the present disclosure in contact with and underneath such a topsheet has been found to give a smaller wetting zone on the topsheet.

The thickness under load of the intermediate layer may be at least about 0.5 mm, such as at least about 1 mm, such as at least about 1.5 mm. The thickness under load of the acquisition layer may also be from about 0.5 mm to about 30 mm, and is measured according to EDANA method WSP 120.6, according to method option A, wherein the thickness is measured after removing one layer of material from a slitted roll, the material being conditioned 30 minutes before measuring. The pressure used was 0.5 kPa with a presser-foot having an area of 25 cm$^2$ and with 10 s waiting before taking the thickness value.

The basis weight of the intermediate layer may be between at least 20 g/m$^2$, such as at least 40 g/m$^2$, such as from 40 g/m$^2$ to 150 g/m$^2$, such as from 40 g/m$^2$ to 100 g/m$^2$.

The thickness and the basis weight of the intermediate layer are of importance to ensure that the acquisition layer provides a sufficiently open and thick structure. This open, thick structure lacking intrinsic absorption capacity contributes to minimizing the wetting zone of the topsheet after wetting. It may also act as a non-absorbing reservoir for temporary liquid containment, which enables liquid in the acquisition layer to rewet to the topsheet to some extent whereby exchange of pH properties with the liquid on the topsheet surface may take place, which promotes a beneficial acidity on the topsheet surface.

The term "non-absorbent fibers" refers to fibers which do not absorb water to an appreciable extent. Suitable polymers from which the non-absorbent fibers may be formed are non-water-absorbent polymers such as polyolefins, polyesters, polyamides and blends and combinations thereof. The non-absorbent fibers may be monocomponent fibers, bicomponent fibers or multicomponent fibers comprising polyolefins, polyesters, polyamides and blends and combinations thereof.

By that the fibrous intermediate layer or the topsheet material "essentially" consist of non-absorbent fibers means that at least 95% of the fibers are non-absorbent fibers, such as at least 99%, such as at least 100% of the fibers in the intermediate layer or the topsheet material are non-absorbent fibers. The acquisition layer and the topsheet material may however also include further substances present in small amounts, such as for example binders and pigments, as known by the person skilled in the art.

As used herein, the term "dry coating" refers to a coating being formed on a material by application of a composition being applied to a web material in a liquid carrier being liquid in room temperature, such as an aqueous solution, followed by drying of the web material, thereby resulting in a dry coating formed on the web material. A "dry" coating, as referred to herein, relates to a coating that has a water content not significantly exceeding the level of water being inevitable due to an equilibrium between the coating and the surrounding atmosphere.

The dry coating may be provided on said topsheet at a concentration 0.1 g to 10 g, such as from 0.3 g to 7 g of said at least one lactone per m$^2$ of the coated area of said topsheet.

When the dry coating is provided on the topsheet material, it is at least present on the at least the side of the topsheet facing away from the absorbent core, i.e. the wearer facing side of the topsheet, on the side of the topsheet facing the absorbent core, i.e. the garment facing side of the topsheet, or on both. When the topsheet material is a fibrous material, e.g. a nonwoven, the coating may essentially be as a layer around the at least part of the circumference of the individual fibers.

When the dry coating is provided on the intermediate layer, it may be provided at a concentration 0.1 g to 10 g, such as from 0.3 to 7 g of said at least one lactone per m$^2$ of the coated area of said layer.

When the dry coating is provided on the intermediate layer, it is at least present on at least the side facing away from the absorbent core, i.e. the wearer facing side of the intermediate layer, on the side of the intermediate layer facing the absorbent core, i.e. the garment facing side of the intermediate layer, or on both. When the intermediate layer is a fibrous material, e.g. a nonwoven, the coating may essentially be arranged as a layer around the circumference of the individual fibers. When the absorbent core is free from water-swellable material, and therefore retains liquid mainly on the basis of capillary forces, the dry coating is typically provided on the topsheet, and the absorbent article does typically not contain any intermediate layer between the absorbent core and the topsheet.

The dry coating according to the present disclosure comprises at least one lactone selected from the group of γ- and δ-lactones, i.e. lactones with 5- or 6-membered rings. The lactones may be saturated or unsaturated.

A function of the at least one lactone in the dry coating according to the present disclosure is to maintain natural skin pH or to adjust the pH to a beneficial value and thus being beneficial for intimate skin health. This may be achieved by use of a sanitary article in accordance with the present disclosure since the lactone thereof is coated onto the topsheet which is the material layer being in direct contact with the skin of the user and/or onto the intermediate layer that is separated from the body only by the topsheet, and therefore may contribute to a suitable pH on the topsheet In presence of water, the lactone exists in an equilibrium between the lactone form and its corresponding hydroxycarboxylic acid form, thereby providing a pH adjusting effect. It is believed that the transfer of the lactone or corresponding hydroxycarboxylic acid thereof may occur both as dry transfer from the coating being in contact with the skin and as wet transfer by means of the bodily fluids being in contact with the coating and also with the skin and the environment between the topsheet and the user skin.

Hereinafter, the term "lactone" refers to the equilibrium system of the compound in the lactone ring form and the hydroxycarboxylic form.

While lactones may exist in different stereoisomeric forms, for the purposes of the present disclosure, all isomeric forms of lactones are considered to be included under this term.

According to an embodiment, a lactone for use in accordance with the present invention is gluconolactone, specifically D-glucono-δ-lactone, which is formed by intramolecular esterification of gluconic acid. The at least one lactone may therefore be, or to a major portion comprise, gluconolactone, e.g. D-glucono-δ-lactone.

The at least one lactone may constitute from 40 to 100 wt %, such as at least 50 wt %, for example at least 75 wt % of the dry coating.

In addition to the lactone, the dry coating composition may further comprise a surfactant. A surfactant according to the present disclosure is a substance which lowers the surface tension of the medium in which it is dissolved, and/or the interfacial tension with other phases, and, accordingly, is positively adsorbed at the liquid/solid and/or at other interfaces. The surfactant may be any known surface active agent suitable for use in hygienic applications, as is generally known in the art. Suitable surface active agents may include any cationic surfactant, anionic surfactant, nonionic surfactant, zwitterionic surfactant or surfactant of amine oxide type suitable for use in hygienic applications and should lower the surface tension of the aqueous solution to allow the solution to spread more easily over the topsheet. This is especially relevant for topsheet materials comprising a high amount of or entirely consisting of synthetic fibers and thus being mainly hydrophobic. In an embodiment, a hydrophobic topsheet material may be used due to the reduced wetting zone after wetting of the topsheet.

Non-limiting examples of suitable surface active agents are; Silastol PHP26, Silastol PHP 28, Silastol PHP 163, Silastol PHP 207 (Schill & Seilacher GmbH), Stantex S 6327 (Cognis), Duron OS 1547, Duron OF 4012 (CHT/BEZEMA), Nuwet 237* and Nuwet 550 (Momentive).

The surfactant may be added to the topsheet or the intermediate layer at a concentration sufficient for it to exhibit the desired effect, and may for example be up to 1 wt %, such as from 0.1 to 0.8 wt % based on the weight of the untreated weight of the topsheet or intermediate layer, i.e. before application of the dry coating.

In addition to the lactone and the optional surfactant, the dry coating composition may further comprise a water soluble polymer.

Non-limiting examples of such water soluble polymers include polyacrylamide and copolymers thereof, polyvinyl alcohols, polyacrylic acids and copolymers thereof, polyalkylene glycols, polyamines, polyethyleneimines, polymeric quaternary ammonium compounds, polyvinylpyrrolidone and copolymers thereof, polyvinyl methyl ether/maleic anhydrides, polysaccharides and mixtures of two or more thereof.

Inclusion of a water soluble polymer into the dry coating may cause the low pH at the topsheet to be maintained for a prolonged time during storage, thereby prolonging the shelf life of the absorbent articles in accordance with the present disclosure.

Herein a polymer will be defined as water soluble, if after adding 1% by weight of polymer to ddH2O water (double distilled water) with stirring at 25° C., adjustment of the pH to a value of 6-7, using NaOH or HCl as appropriate, and after further stirring for 1 hour at said temperature, at least 90% by weight of the added polymer is dissolved in the water.

The water soluble polymers for use in accordance with the present disclosure may have a weight average molecular weight of from about 5,000 Da to 1,000,000 Da, such as from 10,000 to 500,000 Da, for example from 20,000 to 100,000 Da.

The water soluble polymer may be present in the topsheet dry coating in an amount of from 0.05 to 10, or from 0.1 to 5, or from 0.3 to 3 g/m$^2$ of the topsheet.

The dry coating may be substantially free from compounds selected from the list of salts of carbonates and bicarbonates, alkaline peroxides, and azides. It is recognized that a combination of such compounds and lactones may react upon contact with water to form a gas, and such gas formation is not desired in accordance with the present disclosure.

The dry coating maybe essentially homogenously applied on the topsheet and/or an intermediate layer, or may be applied in a patterned manner, covering only part of the surface of the layer on which it is applied. It is contemplated that in one and the same product, the dry coating may be homogeneously applied on one of the topsheet and the intermediate layer, and applied in a patterned manner on the other one of the topsheet and the intermediate layer.

When applied in a patterned manner, the dry coating may for example cover at least 10 area-%, such as from 10 to 90 area-% of the layer on which the coating is applied. For example, the dry coating may be applied regionally to parts of the topsheet that is intended to be in contact with skin especially benefited from the pH-lowering effect of the lactone component in the coating.

The absorbent article in accordance with the present disclosure may, due to the lactone-containing dry coating, exhibit at its topsheet a pH of from 2.5 to 5.5, such as from 3 to 5. The pH at the topsheet is measured as described in the experimental section, and is measured on an area of the topsheet coated with the dry coating, or an area of the topsheet super positioned on an area of the intermediate layer coated with the dry coating within 4 weeks from production and storage of the product at 23° C. at 50% RH.

When worn as intended, a disposable absorbent article in accordance with the present disclosure may result in an adjustment or maintenance of the pH of the skin in contact with said article at a value of from 3.5 to 5.5, according to the method of measuring skin pH as disclosed herein.

Without being bound to any specific theory, it is believed that adjusting skin pH to, or maintaining skin pH within this range is beneficial for the skin health and may help to prevent e.g. *Candida* infections.

The present disclosure also relates to a method for the production of a disposable absorbent article as defined herein. Methods for production of an absorbent product in general will vary between different types of absorbent products and are generally known to those skilled in the art. Generally, such a method comprises disposing an absorbent core between a liquid permeable topsheet and a backsheet, and optionally disposing a liquid permeable and non-absorbing layer, i.e. an intermediate layer between said topsheet and said absorbent core, wherein at least one of the topsheet and the optionally present intermediate layer is provided with a dry coating comprising at least one lactone selected from the group consisting of γ- and δ-lactones.

The topsheet and/or intermediate layer provided with the dry coating may be produced by providing a liquid permeable web material; applying a liquid composition comprising the at least one lactone to the web material and thereafter drying the liquid composition applied to the web material in order to obtain a dry coating on the web material. The present disclosure also relates to the topsheet material as such as described herein, e.g. a liquid permeable non-woven material or a liquid permeable perforated plastic film provided with the dry coating comprising at least one lactone selected from the group consisting of γ- and δ-lactones.

The lactone containing liquid composition may be applied to the web material by any suitable means, including spraying, slot coating, kiss roll coating and/or soaking the material in a bath containing the coating composition, as well as by printing the composition onto the web material by contact or non-contact printing methods known to the person skilled in the art. The coating may be performed in-line during assembly of the absorbent article. Alternatively, the topsheet material may be prepared separately and delivered as ready-to-use rolls to the absorbent article manufacturing plant. The coating may also be formed by a combination of the above methods.

When the dry coating contains further components besides the at least one lactone, such as for example a surfactant and/or a water-soluble polymer, each component may be added to the web material in a single coating step, or may be applied in separate steps to the web material. For example, the web material may be pretreated with surfactant before the application of the lactone, or the lactone may be applied simultaneously with the surfactant.

EXAMPLES

Benefits of absorbent articles in accordance with the present disclosure will now be described with reference to the following non-limiting examples.

Example 1: pH Stability

In this example pH was measured on top-sheet of an absorbent product, directly and at several occasions during six week storage in room temperature. Products with gluconolactone was compared to a product with lactic acid. It was shown that gluconolactone will generate a low pH, and that the pH-lowering effect of gluconolactone is more storage stable compared to that of lactic acid when used on a topsheet layer of an absorbent product.

Test Method for Measuring pH of the Topsheet

The pH of the surface of the products was measured using a pH meter (PH-METER, VWR™ SYMPHONY, SB 80PI and the pH electrode used was HAMILTON FLATTRODE).

The pH meter rod was rinsed with deionized water before each new measurement,

The rinsing of the pH electrode left a small droplet of water hanging from the electrode, which droplet was used to wet the nonwoven web material at the point of measurement. All the pH measurements were performed at 23° C. and approx. 50% RH.

Materials Used

Nonwoven with Lactic Acid:

Nonwoven with wetting agent (standard PP/spun bond/17 g/m$^2$, PHP26 cationic surfactant (approx. 0.15% by weight)), commercially available from Berry Plastic and the addition of buffered lactic acid (Lactic acid/Sodium Lactate, available from Corbion in a 1% w/w solution with pH of 3.2 measured). The nonwoven was dried in room temperature and the amount was measured to be 0.8 g/m$^2$ dry lactic acid on the nonwoven material.

Nonwoven with Gluconolactone:

Nonwoven with wetting agent (standard pp/spun bond/17 g/m2, PHP26 cationic surfactant (approx. 0.15% by weight)), commercially available from Berry Plastic and the addition of gluconolactone (Sigma Aldrich, 1% or 10% water solution, sprayed). The nonwovens were dried in room temperature and the amount was measured to be 0.3 and 4.1 g/m$^2$ dry gluconolactone on the nonwoven material, respectively.

Product Concept:

The nonwovens with added lactic acid or gluconolactone were placed on top of an airlaid and an absorbent core containing cellulose fibers and SAP (30%), The size of these concepts was approximately 10×30 cm.

Storage of the Product Concepts

The products were stored covered with plastic trays in room temperature for 6 weeks.

Results

Results from the pH measurements are shown below the table 1.

TABLE 1

| Added substance | Amount (dry weight g/m2) | pH (0 w) | pH (1 w) | pH (2 w) | pH (3 w) | pH (4 w) | pH (6 w) |
|---|---|---|---|---|---|---|---|
| Lactic acid | 0.8 | 3.9 | 5.9 | 6.4 | 6.8 | 6.4 | 7.3 |
| Gluconolactone | 0.3 | 3.4 | 3.7 | 3.7 | 3.4 | 3.2 | 4.0 |
| Gluconolactone | 4.1 | 3.3 | 2.9 | 2.8 | 3.0 | 2.8 | 3.2 |

From the results above, it is apparent that a dry coating of gluconolactone on the topsheet maintains a low pH more stably than a corresponding dry coating of lactic acid.

Example 2: pH Adjustments on Skin

In this example a top-sheet nonwoven with gluconolactone was wiped against the volar forearm of two volunteers and the change in pH was measured. It was shown that the short contact from wiping decreased the measured skin pH Test Method for Measuring pH of the Skin The pH of the skin was measured using a pH meter (PH-METER, WVR™ SYMPHONY, SB 80PI and the pH electrode used was HAMILTON FLATTRODE).

The pH meter rod was rinsed with saline solution (0.9% NaCl) before each new measurement, The rinsing of the pH electrode left a small droplet of saline hanging from the electrode, which droplet was used to wet the skin on the volar forearm at the point of measurement. All the pH measurements were performed in a climatized room, at 23° C. and 50% RH.

Materials Used

Nonwoven with Gluconolactone:

Nonwoven with wetting agent (standard pp/spun bond/17 g/m$^2$, PHP26 cationic surfactant (approx. 0.15% by weight)), commercially available from Berry Plastic and the addition of gluconolactone (Sigma Aldrich, 10% water solution, sprayed). The nonwoven was dried in room temperature and the amount was measured to be 4.1 g/m$^2$ dry gluconolactone on the nonwoven material.

pH Adjustments on Skin pH was measured on the forearm of two volunteers. Thereafter the gluconolactone treated nonwoven was wiped manually two times over a spot close to the measured reference spot. Table 2 below shows the measured pH on the volar forearms before and after wiping with the gluconolactone nonwoven.

TABLE 2

| Person | Initial pH on the reference spot | pH after wiping with gluconolactone treated NW |
|---|---|---|
| 1 | 5.7 | 4.5 |
| 2 | 5.4 | 3.7 |

From the results above, it is apparent that a gluconolactone coated nonwoven can be used to lower the pH of skin.

The invention claimed is:

1. A disposable absorbent hygiene article, comprising a liquid permeable topsheet, a backsheet and an absorbent core disposed between the topsheet and the backsheet, wherein:
   (a) a liquid permeable and nonabsorbent layer is disposed between said topsheet and said absorbent core and wherein at least one layer, selected from said topsheet and said liquid permeable and nonabsorbent layer, is provided with a dry coating comprising at least one lactone selected from the group consisting of γ- and δ-lactones; or (b) said topsheet is provided with a dry coating comprising at least one lactone selected from the group consisting of γ- and δ-lactones.

2. The article according to claim 1, wherein said liquid permeable and nonabsorbent layer is disposed between said topsheet and said absorbent core and abuts said topsheet.

3. The article according to claim 1, where the dry coating is provided on said topsheet at a concentration of from 0.1 g to 10 g, of said at least one lactone per $m^2$ of the coated area of said topsheet.

4. The article according to claim 1, wherein said dry coating is provided on at least the side of the topsheet facing away from the absorbent core.

5. The article according to claim 1, where the dry coating is provided on said liquid permeable and nonabsorbent layer disposed between said topsheet and said absorbent core at a concentration of from 0.1 g to 10 g of said at least one lactone per $m^2$ of the coated area of said layer.

6. The article according to claim 1, exhibiting at said topsheet a pH of from 2.5 to 5.5.

7. The article according to claim 1, wherein said at least one lactone comprises, or is, gluconolactone.

8. The article according to claim 1, wherein said at least one lactone comprises from 40 to 100 wt % of said dry coating.

9. The article according to claim 1, wherein the dry coating further comprises a surfactant.

10. The article according to claim 1, wherein the dry coating further comprises a water-soluble polymer.

11. The article according to claim 1, wherein said topsheet is a nonwoven web material or a perforated plastic film.

12. The article according to claim 1, wherein said topsheet has a dry basis weight of from 10 to 50 g/m2.

13. The article according to claim 1, wherein said liquid permeable and nonabsorbent layer disposed between said topsheet and said absorbent core is a nonwoven web material.

14. The article according to claim 1, wherein said liquid permeable and nonabsorbent layer disposed between said topsheet and said absorbent core has a dry basis weight of from 20 to 150 g/m2.

15. The article according to claim 1, wherein said dry coating is substantially free from compounds selected from the group consisting of salts of carbonates and bicarbonates, alkaline peroxides, azides, and mixtures thereof.

16. The article according to claim 1, wherein said absorbent core comprises from 10 to 100 wt % of super absorbent polymer.

17. The article according to claim 1, wherein said backsheet is liquid impermeable and vapor permeable.

18. The article according to claim 1, wherein said dry coating is essentially homogenously distributed on said liquid permeable and nonabsorbent layer or said topsheet.

19. The article according to claim 1, wherein said dry coating is applied in a pattern covering from 10 to 90% of the area of said liquid permeable and nonabsorbent layer or said topsheet.

20. A method of adjusting or maintaining a pH of a skin of a subject in contact with a disposable absorbent article, the method comprising contacting the skin of the subject with the disposable absorbent article as defined in claim 1 thereby adjusting or maintaining the pH of the skin of the subject in contact with said article at a value of from 3.5 to 5.5.

21. A method for the production of the disposable absorbent article as defined in claim 1, comprising:

(a) disposing an absorbent core between a liquid permeable topsheet and a backsheet, and disposing a liquid permeable and nonabsorbing layer between said topsheet and said absorbent core, wherein at least one of said topsheet and said liquid permeable and nonabsorbing layer disposed between said topsheet and said absorbent core is provided with a dry coating comprising at least one lactone selected from the group consisting of γ- and δ-lactones; or (b) disposing an absorbent core between a liquid permeable topsheet and a backsheet, wherein said topsheet is provided with a dry coating comprising at least one lactone selected from the group consisting of γ- and δ-lactones.

22. The method of claim 21, wherein said topsheet is obtained by:

providing a liquid permeable web material of nonwoven or perforated plastic film;

applying to said liquid permeable web material a liquid composition comprising at least one lactone selected from the group consisting of γ- and δ-lactones; and drying said liquid composition to render a dry coating composition on said liquid permeable web material.

23. The method of claim 22, wherein said dry coating further comprises a surfactant, and wherein said surfactant is applied to said liquid permeable web material prior to, or simultaneously with, said at least one lactone.

24. The method according to claim 22, wherein the dry coating further comprises a water soluble polymer, and wherein said water soluble polymer is applied to said liquid permeable web material prior to or simultaneously with said at least one lactone.

25. The method according to claim 21, wherein said liquid permeable and nonabsorbing layer is disposed between said topsheet and said absorbent core and is obtained by:

providing a liquid permeable and nonabsorbing nonwoven web material;

applying to said liquid permeable and nonabsorbing nonwoven web material a liquid composition comprising at least one lactone selected from the group consisting of γ- and δ-lactones; and drying said liquid composition to render a dry coating composition on said liquid permeable and nonabsorbing nonwoven web material.

26. The method of claim 25, wherein said dry coating further comprises a surfactant, and wherein said surfactant is applied to said liquid permeable and nonabsorbing nonwoven web material prior to or simultaneously with said at least one lactone.

27. A liquid permeable web material having a dry coating comprising at least one lactone selected from the group consisting of γ- and δ-lactones.

* * * * *